(12) United States Patent
Kollgaard et al.

(10) Patent No.: US 7,222,514 B2
(45) Date of Patent: May 29, 2007

(54) LAMINATE MATERIAL TESTING METHODS AND SYSTEMS

(75) Inventors: Jeffrey R. Kollgaard, Kent, WA (US); Jeffrey G. Thompson, Kent, WA (US); Barry A. Fetzer, Renton, WA (US); Clyde T. Uyehara, Kent, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/870,962

(22) Filed: Jun. 21, 2004

(65) Prior Publication Data

US 2005/0279171 A1    Dec. 22, 2005

(51) Int. Cl.
*G01N 29/04* (2006.01)
(52) U.S. Cl. .......................................... 73/1.82; 73/588
(58) Field of Classification Search ................. 73/1.82, 73/1.86, 588, 609
See application file for complete search history.

(56) References Cited

U.S. PATENT DOCUMENTS

| | | | | |
|---|---|---|---|---|
| 3,813,926 A | * | 6/1974 | Stubbeman ................... | 73/609 |
| 4,215,583 A | | 8/1980 | Botsco et al. .................. | 73/582 |
| 4,840,066 A | * | 6/1989 | Botsco et al. .................. | 73/620 |
| 4,897,796 A | | 1/1990 | Salvado ....................... | 364/497 |
| 5,163,027 A | * | 11/1992 | Miller et al. .................. | 73/1.86 |
| 5,618,994 A | | 4/1997 | Falsetti ........................ | 73/602 |
| 6,073,477 A | * | 6/2000 | Woodmansee et al. ...... | 73/1.82 |

FOREIGN PATENT DOCUMENTS

DE      29908615       6/2000

OTHER PUBLICATIONS

Imaeva, L.A., et al., "Ultrasound Inspection of Multilayered Cellular Structures Produced By Superplastic Forming And Diffusion Bonding", vol. 15, No. 11, 2001, pp. 895-897.

* cited by examiner

*Primary Examiner*—John E. Chapman
(74) *Attorney, Agent, or Firm*—Baker Hostetler LLP

(57) ABSTRACT

Techniques for ultrasonically evaluating damage to a laminate structure include use of a diagnostic device having at least two modes of operation including a calibration mode and a test mode with the calibration mode providing calibration parameters specific to the laminate structure under test.

20 Claims, 16 Drawing Sheets

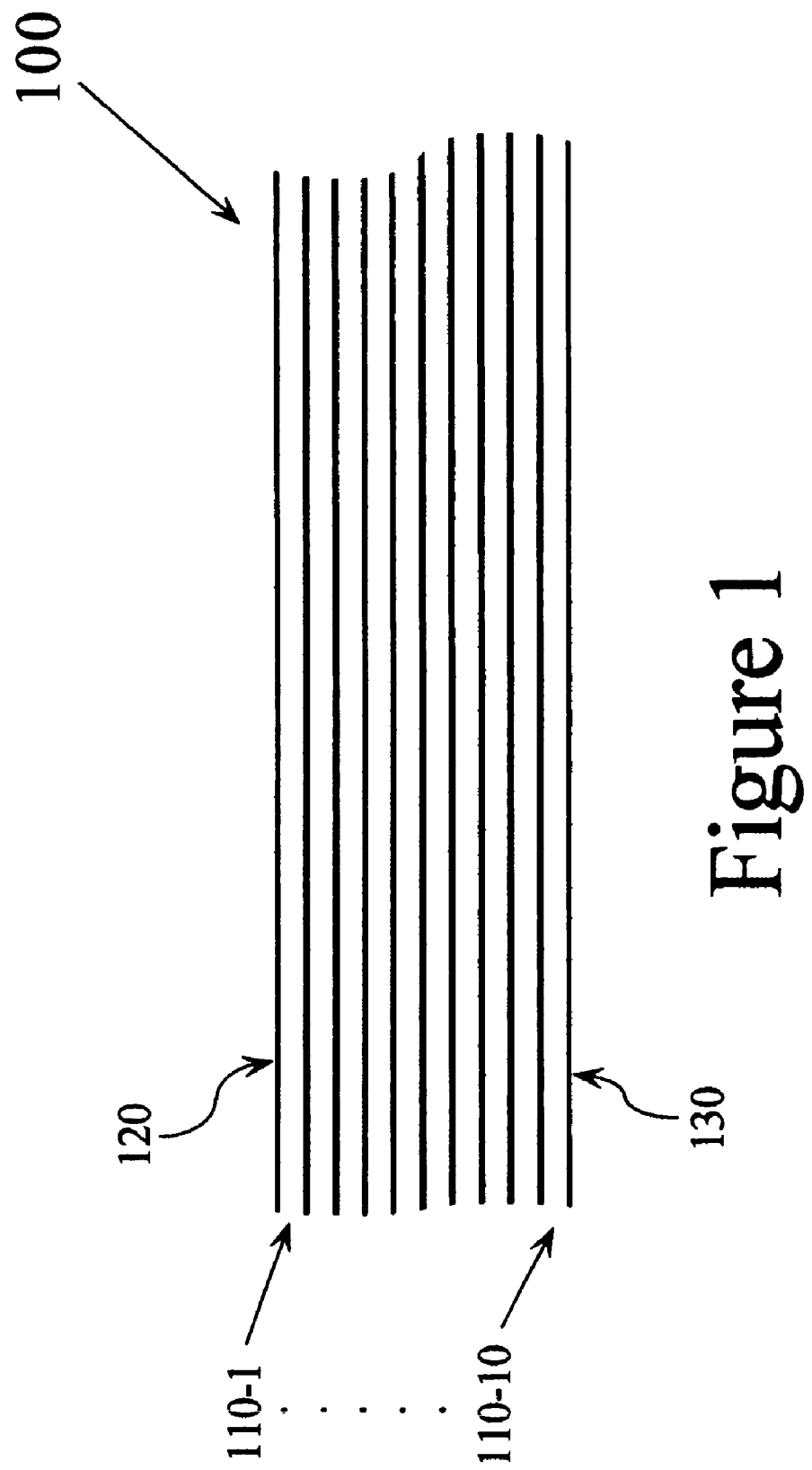

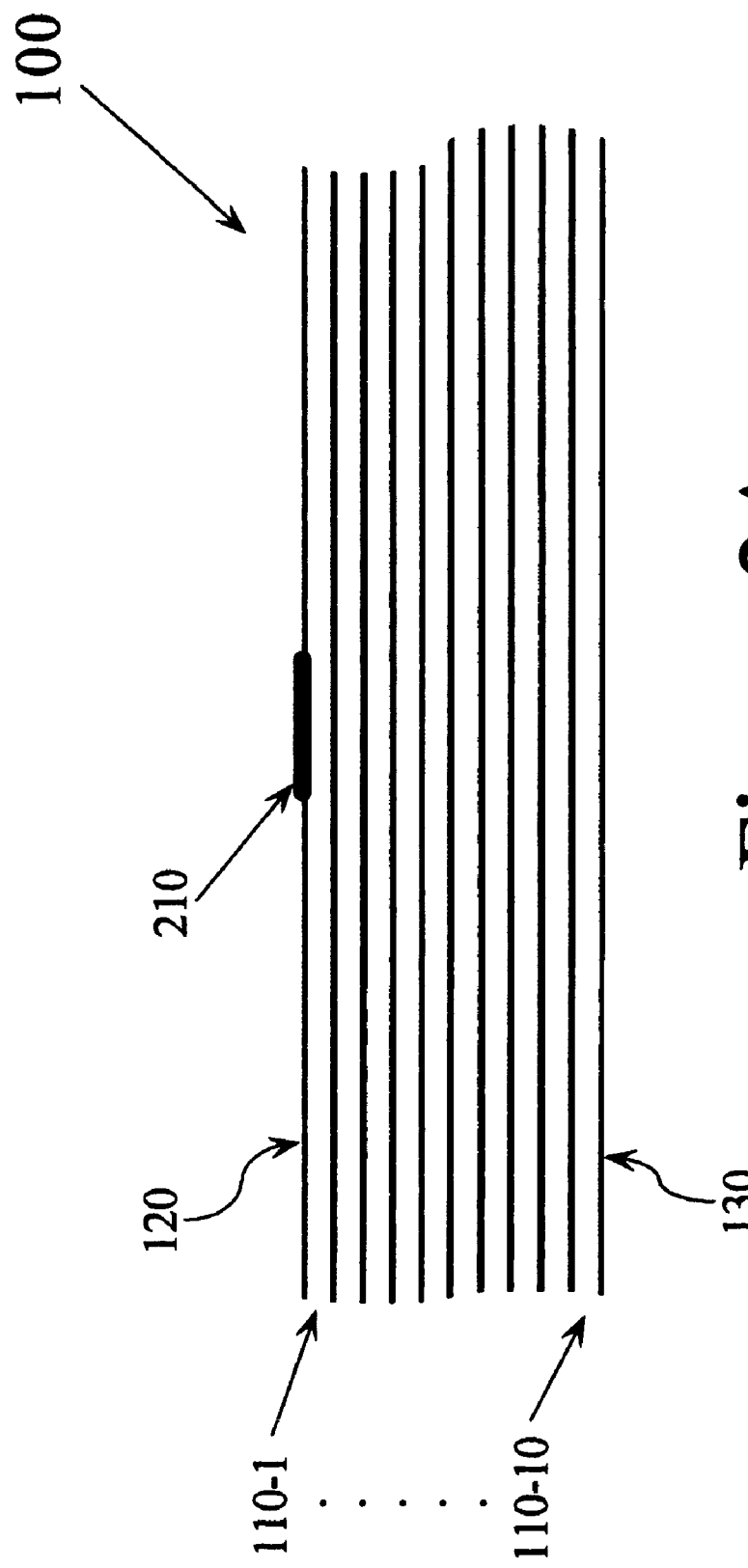

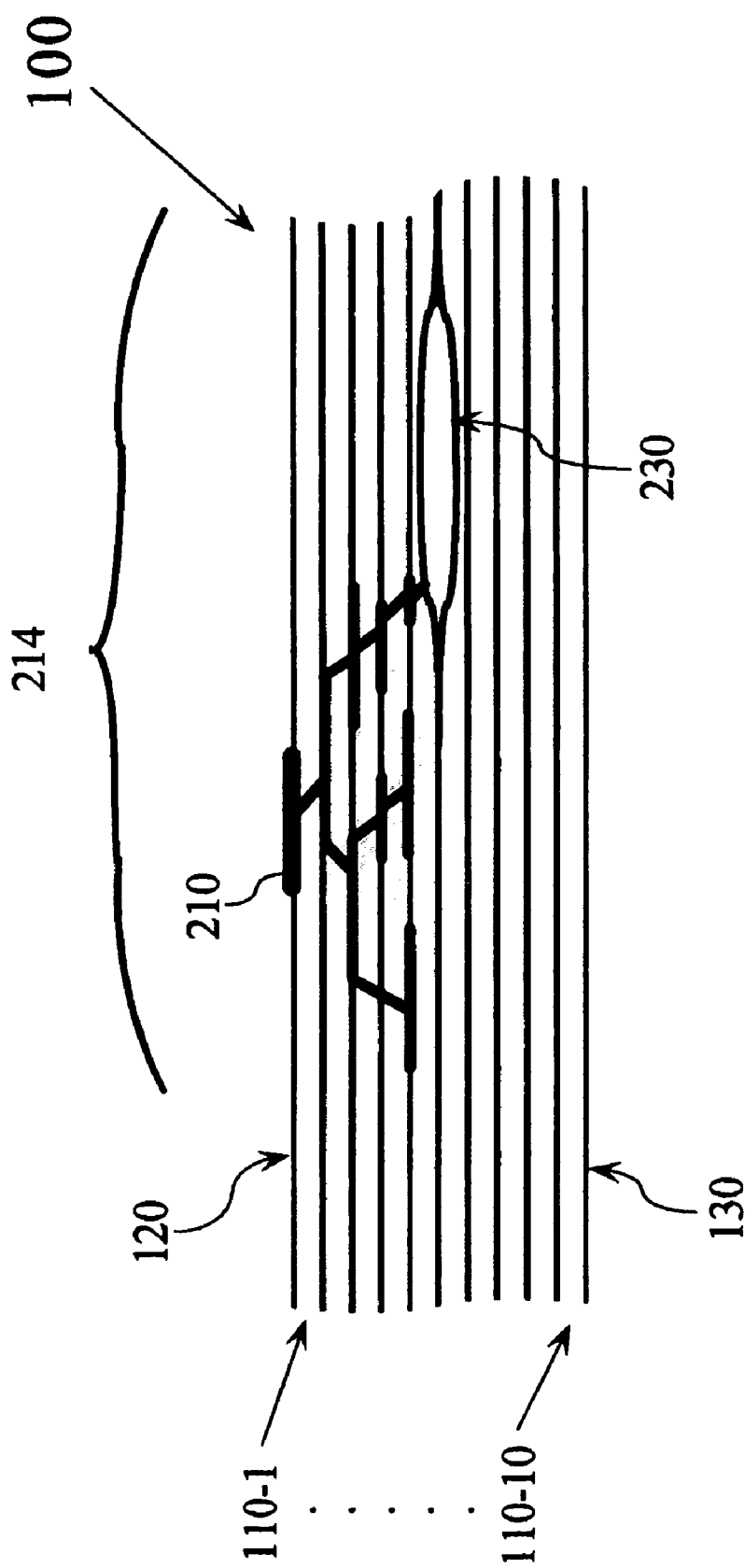

LAMINATE MATERIAL TESTING METHODS AND SYSTEMS

FIELD OF THE INVENTION

This invention relates to methods and systems for non-destructive testing of materials.

BACKGROUND OF THE INVENTION

Originally, naturally available and relatively light materials, such as wood, were the most common materials used for constructing aircraft. However, with the development of new alloys the aircraft construction industry shifted from one of carpentry to one of metal shaping.

Relatively recently, a new generation of materials known as "composites" or "composite materials" were developed. Certain composite materials often provide an excellent strength-to-weight ratio as compared to metals, and their acceptance into the various aircraft industries is near universal.

Generally, there are two major genres of composite materials: honeycomb structures and laminates. Honeycomb structures are exceeding light materials that provide unequalled structural support (for their weight) when placed in wings and other strategic locations in a given aircraft. Laminate materials, while usually not as light as honeycomb structures, are often lighter than any commercially viable metal equivalent, and typically far stronger than any honeycomb structure.

As with all materials, laminates are subject to damage from abuse and high-speed impacts. Unfortunately, the true extent of any resultant damage of a high-speed impact can not always be seen. That is, there are often instances where an impact to a laminate-type structure may only superficially mar its surface, but nonetheless result in extensive damage deep in the laminate's structure where it can not be readily detected. While various diagnostic tools, such as ultrasonic imagers, are available to assess such hidden damage, these existing tools can be very expensive and require a substantial amount of training to properly use. Accordingly, new methods and systems for detecting damage in laminate structures are desirable.

SUMMARY OF THE INVENTION

One of the many advantages of using the below-described approaches is that inexpensive diagnostic equipment can be made that is portable, exceedingly simple to use, yet reliable and accurate.

For example, a method for evaluating damage to a laminate structure having a front-surface and a back-surface is described, the method including calibrating a diagnostic device using an undamaged portion of the laminate structure to determine one or more calibration parameters, and then performing one or more test cycles to a suspect portion of the laminate structure using the one or more of the calibration parameters.

Further, a second method for ultrasonically testing a laminate structure having a front-surface and a back-surface is described that include the steps of performing a test cycle on a suspect portion of the laminate structure based on an ultrasonic echo-profile, and determining whether the suspect portion of the laminate structure conforms to calibration parameters taking into account that the calibration parameters provide information about an undamaged portion of the particular laminate structure under test.

Still further, a method for calibrating a diagnostic device capable of detecting latent damage in a laminate structure is disclosed that includes the steps of emitting an ultrasonic pulse into the laminate structure, detecting an echo-profile of the laminate structure and determining one or more calibration parameters, the calibration parameters providing information about an undamaged portion of the laminate structure under test.

A diagnostic apparatus for evaluating an amount of damage to a laminate structure is also disclosed. In various embodiments, the diagnostic apparatus can include a test manager coupled to a data-acquisition device and a sonic transducer, and configured such that the diagnostic apparatus employs a calibration cycle and a test cycle, the calibration cycle produces one or more calibration parameters, and the test cycle uses the one or more of the calibration parameters to evaluate whether a portion of the laminate structure is damaged.

There has thus been outlined, rather broadly, certain embodiments of the invention in order that the detailed description thereof herein may be better understood, and in order that the present contribution to the art may be better appreciated. There are, of course, additional embodiments of the invention that will be described or referred to below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 depicts an exemplary laminate structure.

FIGS. 2A-2D depict the laminate structure of FIG. 1 with differing amounts of damage.

DETAILED DESCRIPTION

Figure 2B:
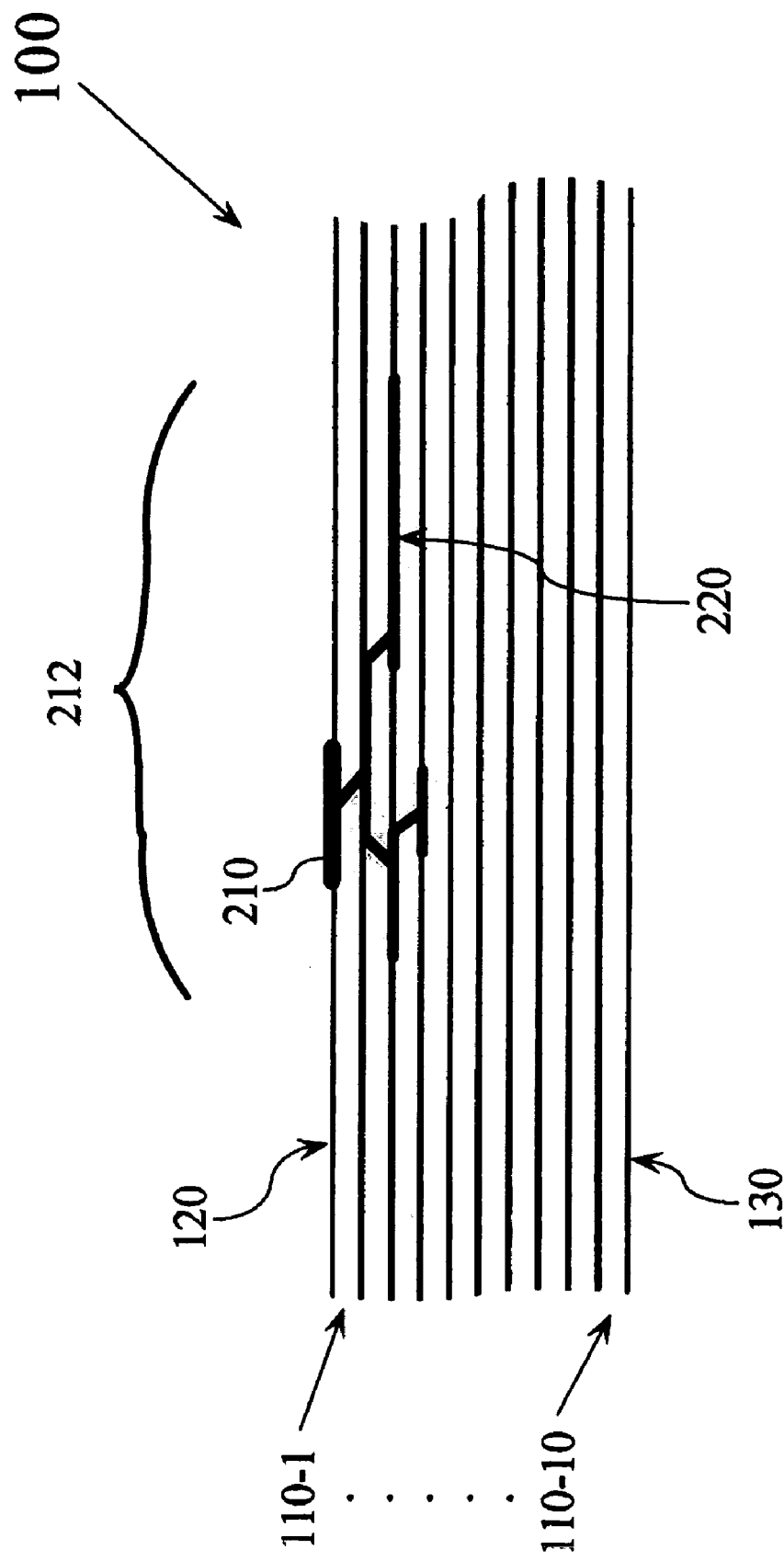

As mentioned above, various diagnostic tools, such as ultrasonic imagers, are available to assess such hidden damage to laminate structures. Unfortunately, such tools are very expensive and require a substantial amount of training to properly use. However, the methods and systems discussed below outline an approach to overcoming the expense and training issues. That is, the below-referenced methods and systems can enable an operator to diagnose hidden damage in a process so simple and straightforward that, in various embodiments, can be reduced to merely touching a small hand-held tool to a structure under test, then referring to the state of a single light emitting diode.

FIG. 1 depicts an exemplary laminate structure 100 capable of being used on any number of structures, such as those found on airplanes, automobiles and other vehicles, or any other structure that can benefit from a light, yet strong material. As shown in FIG. 1, the laminate structure 100 has a front-surface 120 and a back-surface 130 and is composed of ten individual laminate sheets 110-1 to 110-10; such laminate sheets 110-1 to 110-10 being joined together by a compatible bonding material (not shown).

The exemplary laminate sheets 110-1 to 110-10 are composed of sheets of graphite fibers, and the exemplary bonding material (not shown) is composed of an ester based resin. However, it should be appreciated that the particular make up of the laminate sheets 110-1 to 110-10 can vary to incorporate carbon-based fabrics, metal foils, polymer-based fabrics, (e.g., Kevlar) or any other known or latter developed material useful to form laminate structures without departing from the spirit and scope of the present disclosure. Similarly, while the laminate structure 100 of FIG. 1 is formed using an ester-based resin, other bonding materials can also be used based on design choice or as required without departing from the spirit and scope of the present invention.

In the course of normal use, laminate materials are subject to accidental damage. For example, various high-speed aircraft using laminate materials to cover the front surfaces of their wings can expect impact damage from birds and various airborne debris with every flight. Obviously, in some instances the resultant damage will be very light while in other instances the damage may be moderate to severe. For example, as shown in FIG. 2A the laminate structure, 100 of FIG. 1 is depicted as being so lightly damaged that only a superficial marring results at impact site 210.

However, similar impacts may cause damage that may not be readily apparent. For example, as shown in FIG. 2B, the same impact discussed with respect to FIG. 2A may produce a first damaged area 210 that includes identical marring at impact site 210, but further includes the number of hidden fissures, including fissure 220 positioned between laminate sheets 110-2 and 110-3.

Generally, it should be understood that a fissure can be a crack either between two laminate sheets or through a particular laminate sheet that does not result in any open gap. While appearing to be of minor concern, even minor fissures can sometimes represent a substantial threat to the integrity of a laminate structure as laminates derive their strength from their bonded layering.

Still further, as shown in FIG. 2C, an even heaver impact can result in a second damaged area 214, which depicts a traumatized than the substrates 100 depicted in FIGS. 2A and 2B. As shown in FIG. 2C, the second damaged area 210 includes superficial marring 210 (which may still look exactly like the superficial marring of FIGS. 2A and 2B), a number of fissures and a void 230. In contrast to fissures, a void is a type of damage where two laminate sheets that should be joined now fail to make contact altogether. Voids are sometimes caused when a fissure develops between two individual laminate sheets and at least one laminate sheet is so damaged as to be permanently warped away from the other laminate sheet.

Figure 2D:
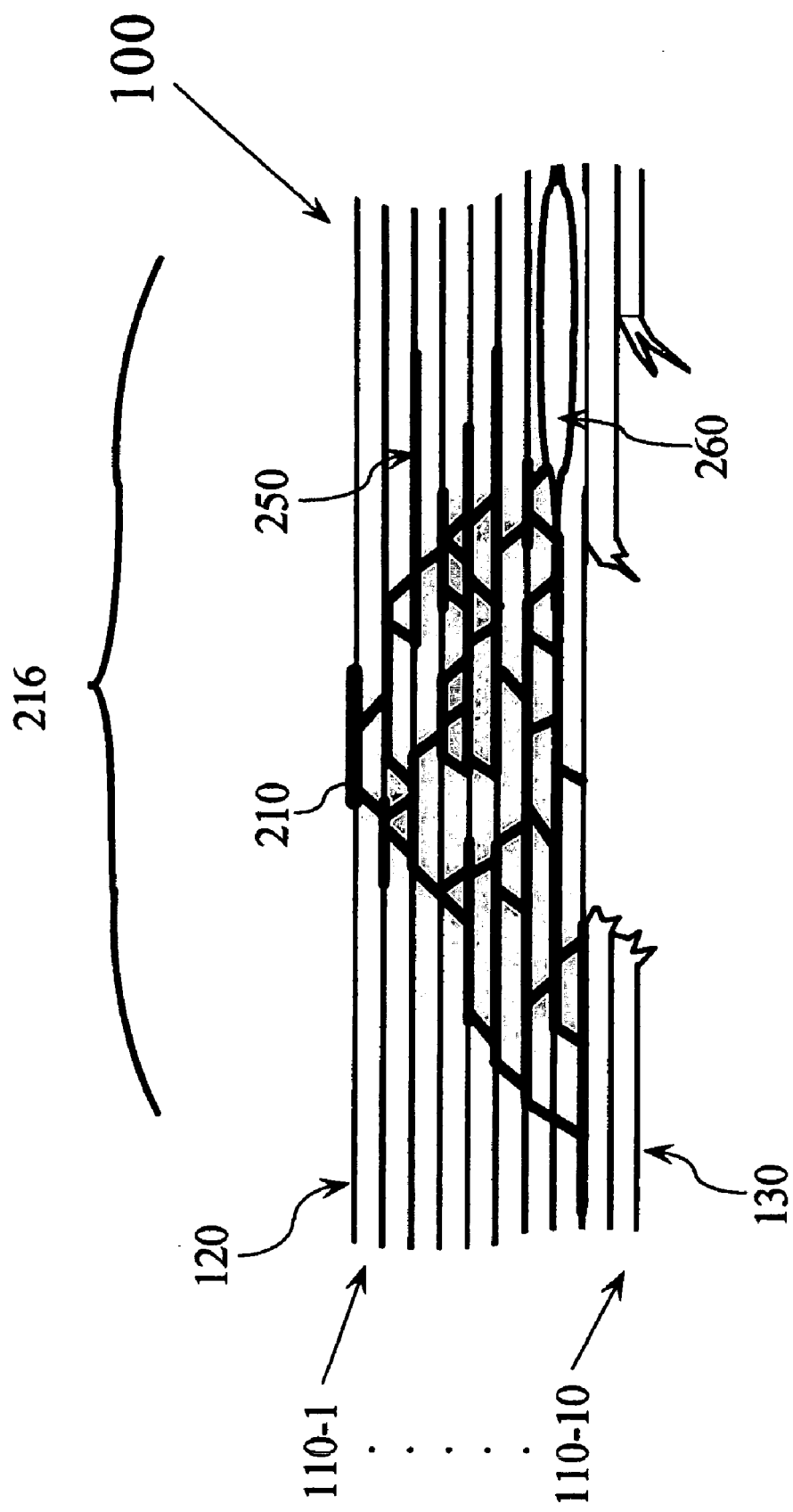

Continuing to FIG. 2D, it should be appreciated that a high-speed impact may leave only a superficial marring on a laminate's surface, but nonetheless result in severe damage below the surface. As shown in FIG. 2D, a third damaged area 216 is depicted as having a superficial marring at impact site 210, a large network of fissures including the fissure 250 and a void 260. As further shown in FIG. 2D, severe hidden damage can result with portions of one or more laminate sheets being entirely ripped away from the back-surface 130.

In view of FIGS. 2A-2D, it should be appreciated that the amount of superficial damage to a laminate structure is a poor indicator of any true amount of hidden damage. Accordingly, it should be appreciated that it is advantageous to have inexpensive yet highly accurate diagnostic tools that can be effectively detect unseen damage to such suspect areas around superficial marrings.

Figure 3:
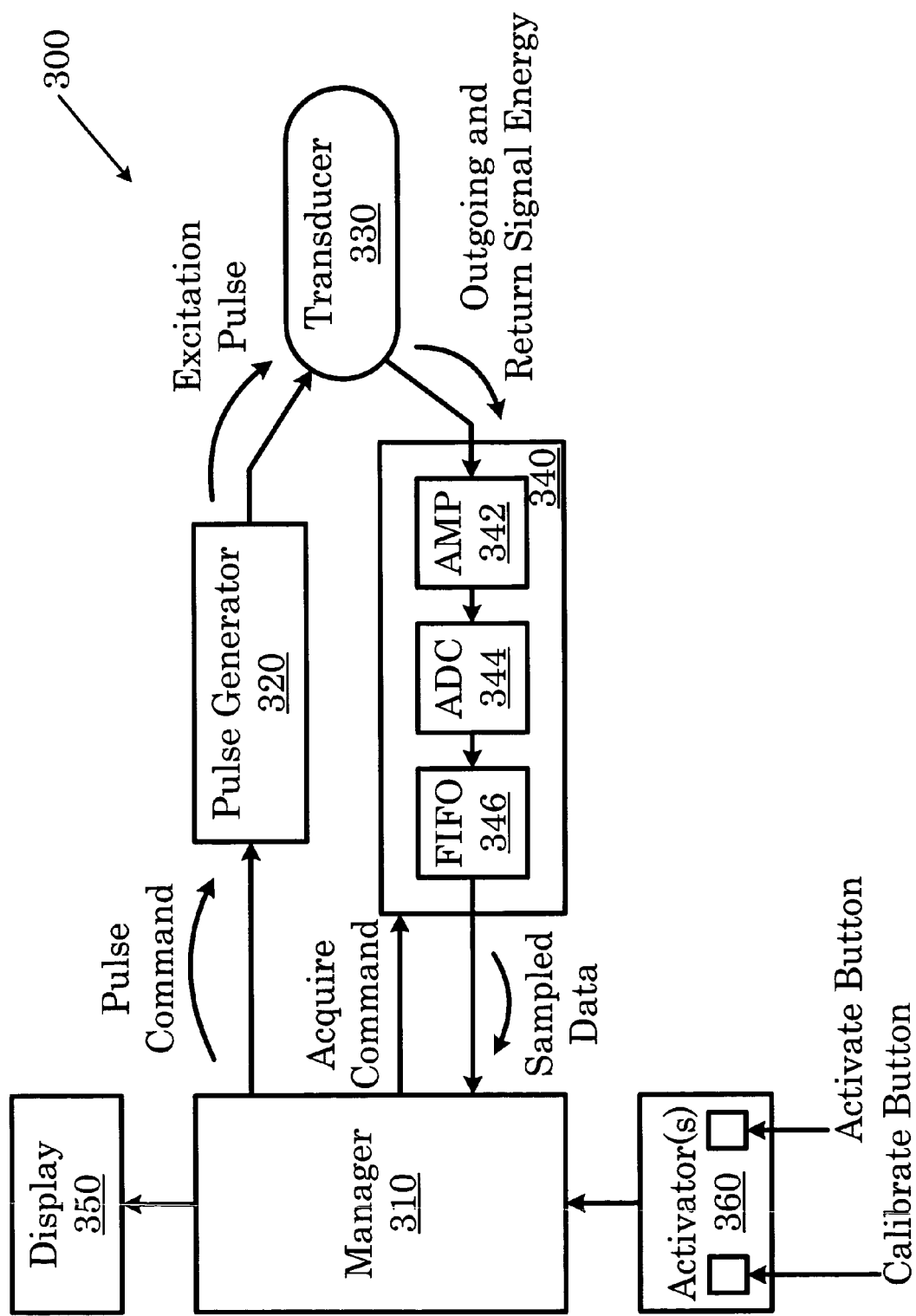
FIG. 3 is a block diagram of a diagnostic tool useful for detecting hidden damage in laminate structures.

FIG. 3 is a block diagram of an exemplary diagnostic tool 300 capable of detecting hidden damage to various solid structures, including laminate structures such as those depicted in FIGS. 1-2D. As shown in FIG. 3, the diagnostic tool 300 includes a manager 310, a pulse generator 320, a transducer 330, a data acquisition device 340, a display 350 and a number of activators 360. The data acquisition device 340 includes an amplifier (AMP) 342, an analog to digital converter (ADC) 344 and a first-end-first-out buffer (FIFO) 346. While the exemplary diagnostic tool 300 is a collection of various integrated circuits and other components coupled together on a single circuit-board, it should be appreciated that, the diagnostic tool 300 can take other forms. For example, in various embodiments, the pulse generator 320, as well as the FIFO 346 and ADC 344 may be incorporated into a bussed structure such as that is commonly used on many processor-based systems. In still other embodiment, it should be appreciated that practically all of the various components 310-360 may be incorporated on a single integrated circuit, with the understanding that any display, transducer or activator might be more practically located off-chip.

For the exemplary diagnostic tool 300 of FIG. 3, there can be two main modes of operation: a calibration mode executing calibration cycles and a test mode executing test cycles.

The calibration mode of diagnostic tool 300 is substantially different from any form of calibration for competing types of test devices in that the diagnostic tool 300 of the present system uses its calibration mode to calibrate itself against a particular laminate structure, as to the more commonly used form of calibration where individual components within a device are "tweaked" (or otherwise compensated for) such that a diagnostic device will have a greater overall accuracy. One of the advantages to calibrating against specific laminates is that it can be far less expensive than the alternative. For example, the diagnostic tool 300 of FIG. 3 can be calibrated by a completely untrained operator by merely pressing the transducer 330 against an undamaged portion of a laminate structure under test. In comparison, the latter form of calibration can require that a particular test device be returned to a factory where trained technicians may spend hours characterizing the various component within the test device any form of compensation may even begin.

To start the compensation cycle, an operator using diagnostic tool 300, can initially press the transducer 320 against an undamaged portion of a substrate and press one of the activators, e.g., a button, which will in turn provide the manager 310 with an indication that a calibration cycle is desired. In response, the manager 310, will generate a command signal to the pulse generator 320. The pulse generator 320, in turn, can receive the command from manager 310 and generate an excitation pulse having a particular amplitude and duration to the transducer 330.

In the exemplary diagnostic tool 300 of FIG. 3, the pulse generator 320 can accept a TTL-compatable signal, such as a low-to-high transition, and generate an excitation pulse having an amplitude of about 25-30 volts and a duration of about 200 nanoseconds. However, it should be appreciated that other types of input commands and the output excitation pulses associated with the pulse generator 320 can change from one embodiment to another.

Once the excitation pulse is initialized, the transducer 330 can receive the excitation pulse, which will cause the transducer 330 to emit a burst of ultrasonic energy to a given structure, with which the transducer 330 makes contact.

During operation, the transducer 330 will perform not only the role of providing an outgoing pulse of ultrasonic energy, but also will detect energy that is echoed back to the transducer. As the transducer 330 detects this of the same frequency returned signal energy, the transducer 330 will transform such ultrasonic energy into an electrical form that can be sensed by any number of electrical or electronic device. Accordingly, it should be understood that the transducer 330 will pass an amount both outgoing and detected signal energy to the data acquisition device 340.

As various signal energies are received by the data acquisition device 340, such energies are first received by the amplifier 342 which can buffer, amplify and filter the received energies, then pass the resultant signal to the ADC 344. The ADC 344, in turn, will convert the received signal to digital form. Subsequently, the digitized data can be passed to FIFO 346, where it can be stored until extracted by manager 310.

After data acquisition has started, the manager 310 can extract information from the FIFO 346, determine any number of calibration parameters, such as parameters relating to the amplitude and timing of any returned pulses, and store such calibration parameters in a local memory for use in a test cycle.

Once a user has performed a calibration cycle with the diagnostic tool 300, the operator can press the transducer portion of the diagnostic tool 300 against a portion of the laminate device that is suspect for hidden damage and press a second activator button. In response, the activator 360 will pass an appropriate signal to manager 310 to start a test cycle. As with the calibration mode, a manager 310 will generate a command to the pulse generator 320, which will in turn generate an excitation pulse of substantially the same amplitude and duration as the excitation pulse of the calibration cycle. In response, the transducer 330 will emit an outgoing ultrasonic signal detect any returned signal energy, and pass the outgoing and detected signals to the data acquisition device 340 and manager 310.

Once the manager 310 has received information regarding the immediate test cycle, the manager can perform any number of operations and calculations necessary to determine whether such data taken during the test cycle substantially conforms within the parameters acquired during the calibration cycle. For example, the manager 310 can compare the amplitude of any return signal pulse and compare it to the return signal pulse of the calibration cycle, and/or the manager can determine whether such a returned signal pulse occurs at substantially the same relative timing (with respect to the outgoing pulse) as the return signal pulse of the calibration cycle. If the data of the test cycle acceptably conforms with the date of the calibration cycle, the manager can provide display 350 with an indication that the suspect laminate structure is undamaged. The display 350, in turn, can receive the indication, and provide an operator with a visible indication that the diagnostic tool did not detect any damage to the suspect area tested.

In the exemplary of embodiment of FIG. 3, the display 350 can include but a single light emitting diode to indicate whether a particular portion of a laminate structure is damaged or undamaged, and optionally include a second light emitting diode to indicate whether the diagnostic tool 300 had been properly calibrated. However, it should be appreciated that while the diagnostic tool 300 requires a far simpler display than any known competing product, the particular form of display chosen for any particular embodiment can vary as a design choice.

Figure 4:
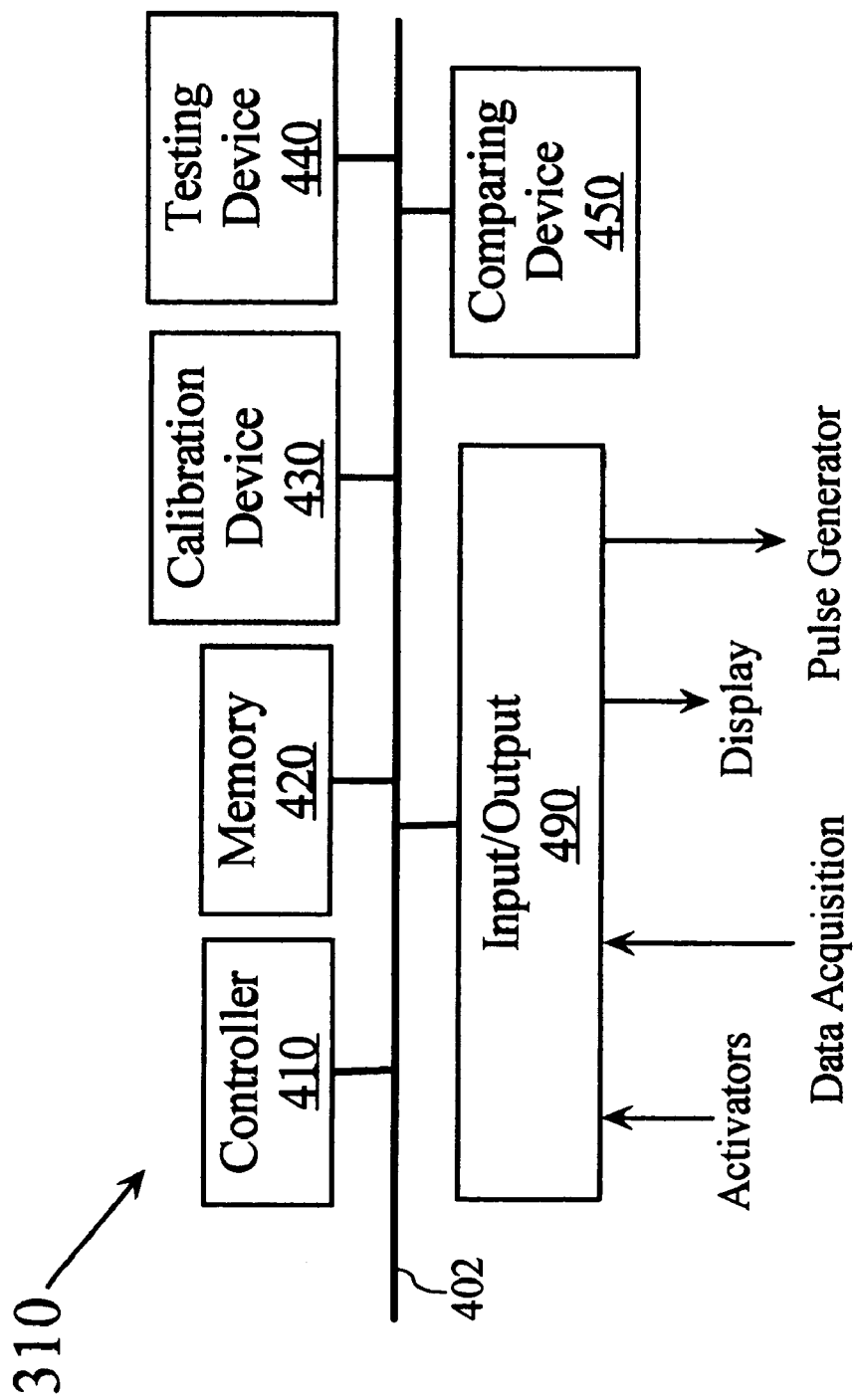
FIG. 4 is a block diagram of an exemplary embodiment of the manager of FIG. 3.

FIG. 4 is a block diagram of an exemplary embodiment of the manager 310 of FIG. 3. As shown in FIG. 4, the manager 310 includes a controller 410, a memory 420, a calibration device 430, a testing device 440, a comparing device 450 and an input/output port 490. The various portions 410-490 of the manager 310 are coupled together via data/address bus 402. While the exemplary manager 310 is depicted as a device having a bussed architecture with various peripherals, it should be appreciated that in other embodiments, the manager 310 can appear as a single-chip processor with integrated components, a general purpose processor, a digital signal processor or any other system capable of executing a series of instructions from a memory. Further, it should be appreciated that the manager 310 can take the form of any number of discreet logic circuits capable of performing the various required functions as described herein. Still further, it should be appreciated that, in various other embodiments, portions of the manager 310, such as the calibration device 430, the testing device 440 and the comparing device 450 can take the form of various programs and routines embedded in memory 420.

In operation, the manager 310 generally starts by coordinating a calibration cycle. In such a calibration cycle, the manager 310 typically receives an indication from an external device, such as a push button, received via the input/output port 490. In response, the manager 310 can then issue a command to a pulse generator system, such as the pulse generator 320 shown in FIG. 3, as well as a "capture data" command to a data capturing system, such as the data acquisition device 340 on FIG. 3. Assuming that the appropriate data has been captured, the controller 410 can subsequently import the captured data via the input/output port 490, and store the captured data in the memory 420.

Subsequent to data import, the controller 410 can then move the data from the memory 420 to the calibration device 430. As the data calibration 430 receives the data, the calibration device 430 can perform any number of operations designed to measure or qualify various aspects of an echo-profile, such as determine the amplitudes of an outgoing and return signal pulse, determine relative timing of pulses, characterize pulse shape information, and phase information, etc.

Generally, for calibration cycles, the calibration device 430 should detect but two appreciable pulses: the outgoing pulse and a return signal pulse that results when the outgoing pulse reflects from a back-surface of a laminate structure, i.e., the "back-surface return pulse." While the back-surface return pulse will generally undergo a certain amount of distortion and otherwise be contaminated with various amounts of noise, it should be appreciated that with the appropriate processing, such distortion and noise can be readily abated or otherwise compensated.

Once the calibration device has performed its initial processing on the outgoing and return pulses, the calibration device can determine the absolute and/or relative amplitude of both pulses as well as the absolute and/or relative timing between pulses, which for the purpose of this disclosure, such amplitude and timing information can be referred to as possible "calibration parameters." Once the calibration device 430 has completed its processing and determined the relevant calibration parameters, the calibration device 430 can send a signal to an external device, such as a light emitting diode, indicating that an appropriate calibration cycle has been completed and that calibration parameters have been established.

It should be noted that in various instances, the outgoing and return signal energy may be corrupted by excessive noise, or various artifact may appear, such as echoes caused by unknown defects, fissures or voids. Assuming that such excessive noise or artifacts do occur during a calibration cycle, the calibration device 430 can be appropriately designed to recognize that received data is problematic and subsequently issue an indication to a display, that a problem with the calibration cycle has occurred. Assuming that an operator receives such an indication, the operator can perform a second calibration cycle on another portion of the subject laminate structure until a good calibration cycle is performed and valid calibration parameters are established.

While the exemplary manager 310 performs a single round of generating an outgoing pulse and detecting return signal energy, in various embodiments the manager 310 can opt to use a plurality of calibration rounds (with appropriate statistical processing) to better determine calibration parameters and qualify any variations of amplitude and timing data for more reliable testing.

As discussed above, during normal operation one or more test cycles will generally be performed after a given calibration cycle. During a test cycle, the process will generally start with an operator providing an indication to the controller 410 via a button (not shown) and input/output port 490. In response, the controller 310, can generate a command to a pulse generator and data acquisition device, then store any resultant data in memory 420.

Subsequently, such test data can be provided to the testing device 440 where such information can be appropriately processed to determine whether any substantially pulses are detected, as well as determine the timing between such pulses occur relative to an initially outpoint pulse. As with the calibration cycle, the testing cycle can be accomplished with a single round of pulses with multiple rounds.

Once the calibration device 430 and the testing device 440 have both performed their respective task to identify various peak energy points and timing information such data can be delivered to the comparing device 450.

The comparing device 450 can receive the calibration parameters from the calibration device 430, as well as the testing data from the testing device 440, and perform any number of operations necessary to determine whether the test data appropriately conforms to the calibration data. For example, in the exemplary embodiment the comparing device 450 will determine whether the return pulse of a test cycle occurs within a defined, usually narrow time range centered on the respective timing parameter, and further determine whether the amplitude of such a return pulse is approximately the same, e.g., within 10%, of the return pulse of the calibration cycle. Assuming that the back-surface return pulse measured during a testing cycle adequately conforms with the return pulse of a calibration cycle, the comparing device 450 can send a signal to an indicator, such as a "damage/undamaged" indicator via input/output port 490.

While in a various embodiments, a damaged/undamaged indication can be made using only data relating to a single back-surface return pulse, it should be appreciated that in other embodiments, the comparing device 450 may use other criteria to make its determination. For example, in various embodiments the comparing device 450 may look for any number of substantial pulses that may occur between an outpoint pulse and a back side return pulse, the amount and nature of any noise present or any other aspect of an echo-profile that can be detected. Accordingly, it should be appreciated that the number and nature of calibration parameters will change as different data is used. That is, while in some embodiments a set of calibration parameters can include but one or two numbers representing timing and/or amplitude information, other calibration data can take the form of a complete echo-profile, a statistically derived echo-profile, a Fourier transform of portions of an echo-profile and so on.

Figure 5:
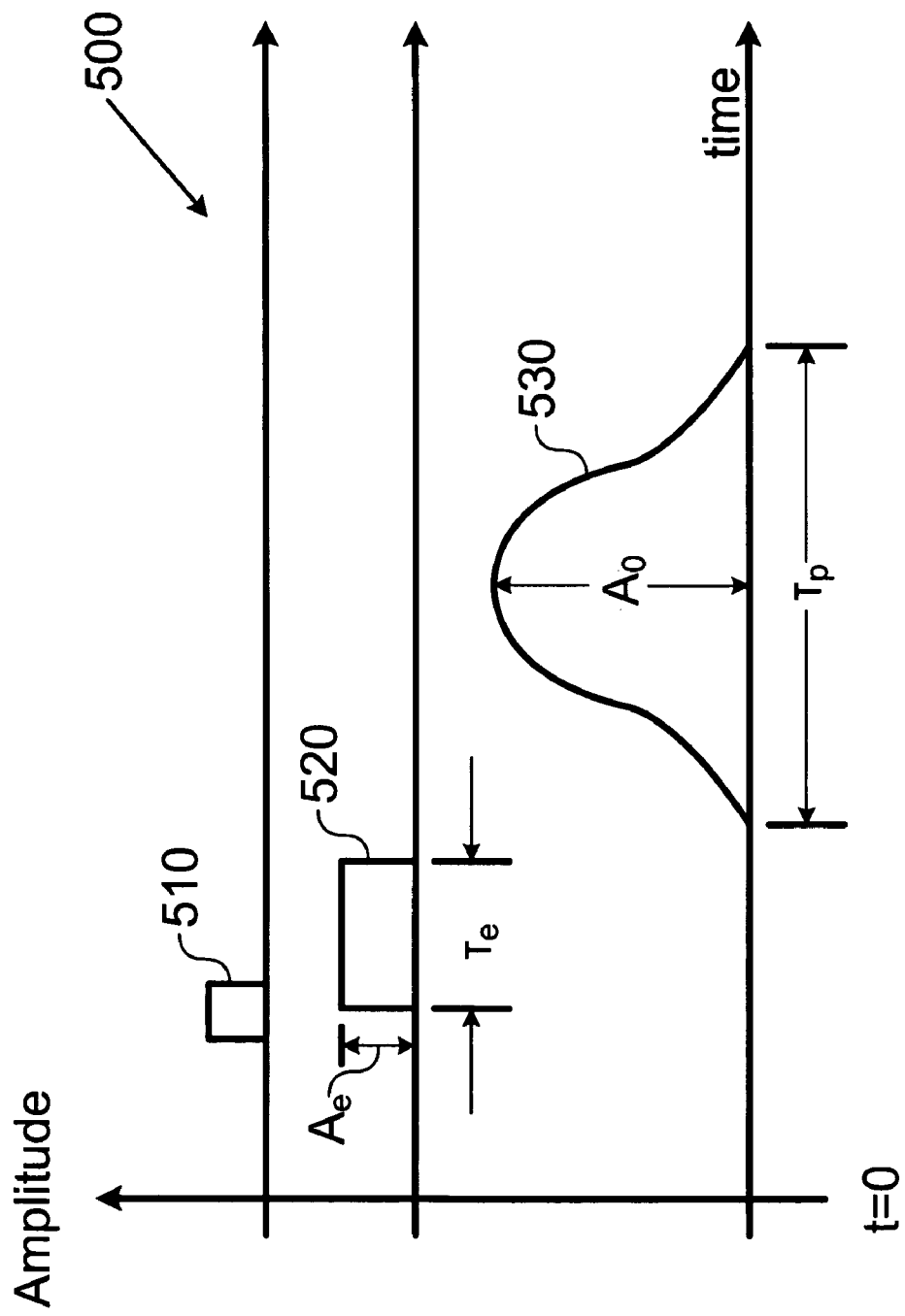
FIG. 5 is a timing diagram of various activities within the diagnostic tool of FIG. 3.

FIG. 5 is a timing diagram depicting the steps taken to generate an outgoing pulse of a transducer such as the ultrasonic transducer 330 of FIG. 3. As shown in FIG. 5, an excitation pulse 520 is depicted as following a command pulse 510. As further shown in FIG. 5, the excitation pulse 520 has an established amplitude $A_e$ as well as a distinct duration $\tau_e$. For the exemplary embodiment of FIG. 3, such an excitation pulse 520 will generally have an amplitude of 25-30 volts and a duration of about 200 nanoseconds. However, it should be appreciated that in various embodiments, the particular amplitude and duration of an excitation pulse can vary as desired or otherwise found advantageous taking into account any number of significant variables, such as the electrical properties and resonant frequency of a transducer.

As is further shown in FIG. 5, a bell-shaped outgoing pulse 530 is depicted as occurring shortly after the excitation pulse 520. While the outgoing pulse 530 is depicted as a smooth bell-shaped pulse, it should be appreciated that the outgoing pulse 530 actually represents an envelope describing an amplitude of a high frequency oscillation occurring within the bell-shaped pulse 530. For example, assuming that the width of the bell-shaped pulse ($\tau_p$) is one microsecond, and further assuming that the transducer used has a resident frequency of five megahertz, the outgoing pulse 530 will actually describe a modulation of four to five cycles of five-megahertz ultrasonic energy with the peak amplitude ($A_O$) occurring about the third cycle.

While the exemplary diagnostic tool 300 of FIG. 3 will generally have an output pulse of one microsecond with a resident frequency of five megahertz, it should be appreciated that in other embodiments, pulse width as well as oscillation frequency can vary depending on the characteristics of the transducer used. For example, in various embodiments the inventors of the systems and methods of this disclosure have determined that a five megahertz ultrasonic transducer works exceedingly well and that a range of frequencies varying from 2.5 megahertz to 10 megahertz are all very good candidates for use with the methods and systems of the present disclosure. While lower frequencies below 2.5 megahertz can also be used, it should be appreciated that such lower frequencies will result in proportional decreases in resolution. Further, while frequencies above 10 megahertz are also viable, higher frequencies will undergo substantial attenuation proportional to frequency increases.

Figure 6A:
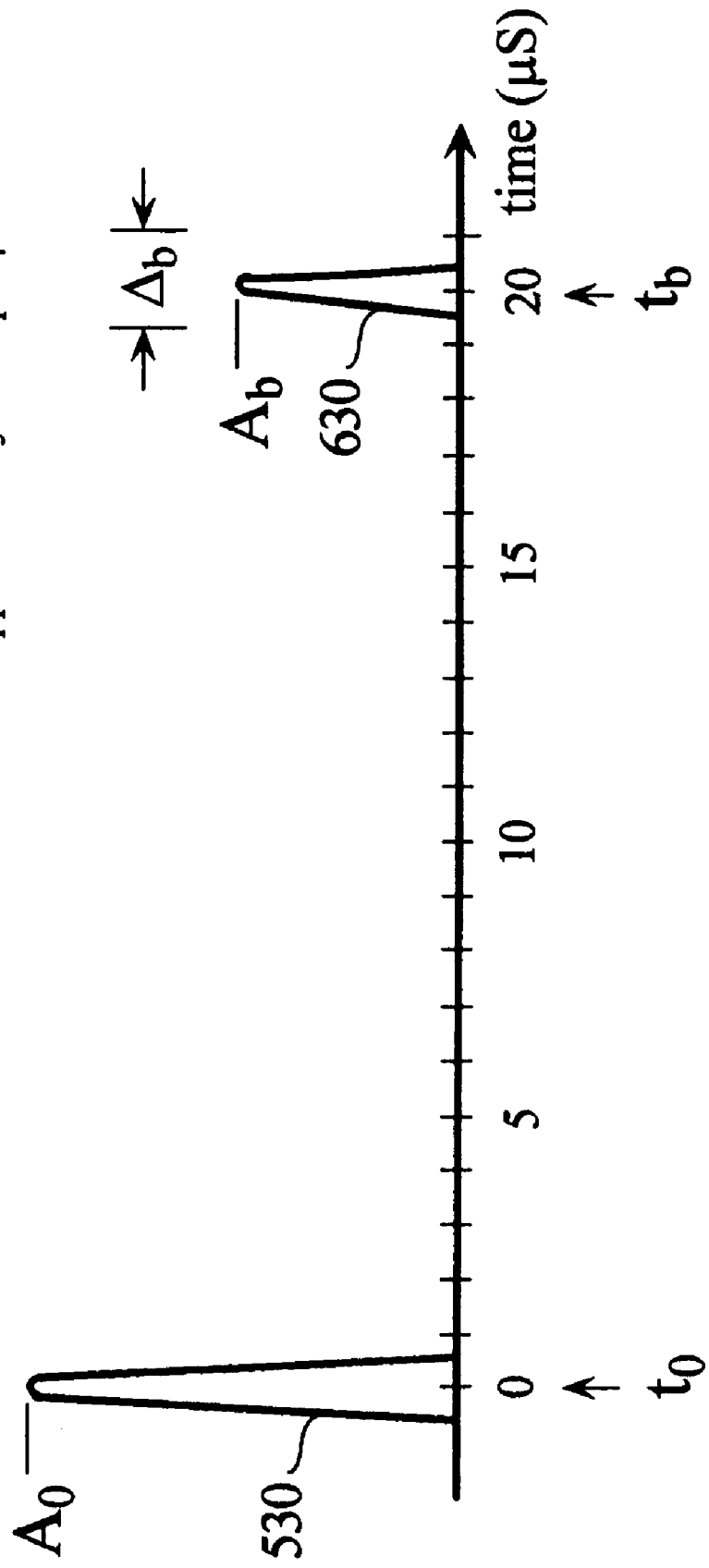
FIGS. 6A-6D are exemplary timing diagrams depicting ultrasonic echo-profiles of the respectively laminates depicted in FIGS. 2A-2D.

FIG. 6A is a first timing diagram of an echo-profile that includes an outgoing and back-surface return pulse of a laminate structure, such as one of the laminate structures shown in FIGS. 1 and 2A. As shown in FIG. 6A, an outgoing pulse having amplitude $A_0$ and centered around time $t_0$ is followed by a back-surface return pulse 630, the back-surface return pulse 630 having an amplitude $A_b$ and occurring at time $t_b$. As the back-surface return pulse 630 is depicted as occurring 20 microseconds after the outgoing pulse 530, it should be appreciated that the laminate structure represented should be approximately 30 mm thick (1¼ inches), assuming that the speed of sound in a solid laminate material is approximately 3 mm/microsecond. Generally, the echo-profile, of FIG. 6A is the desired profile sought in a calibration cycle as well as the profile expected during any testing cycle of an undamaged laminate structure.

Figure 6B:
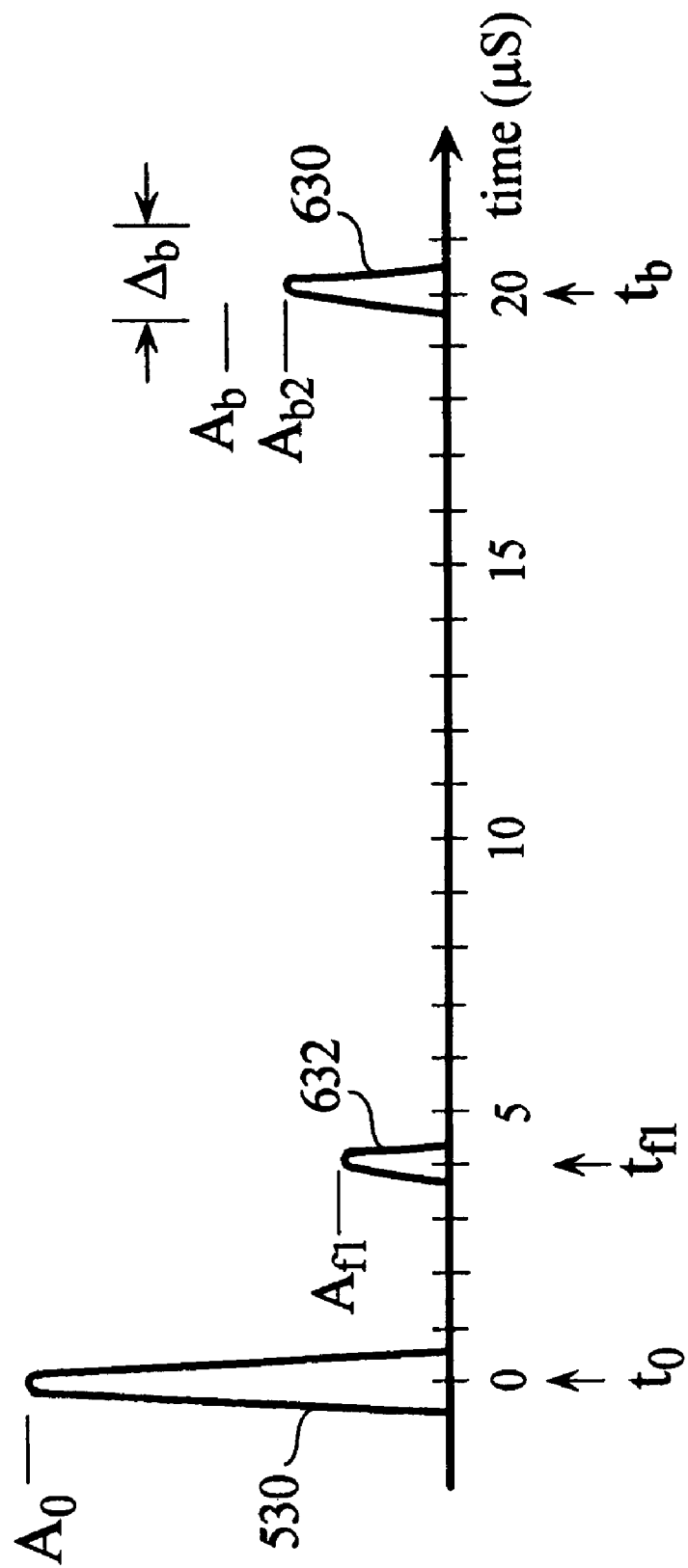

In contrast, FIG. 6B depicts a second timing diagram of an echo-profile as might be expected from the slightly damaged laminate structure shown in FIG. 2B. As shown in FIG. 6B, the echo-profile includes the initial outgoing pulse 530, and expected back-surface return pulse 630 occurring at the same time $t_b$ as the back-surface return pulse of FIG. 6A, but further includes a "fissure return pulse" 632 that (in the present example) is caused by fissure 220 of FIG. 2B. A review of the echo-profile of FIG. 6B reveals that the fissure 220 of FIG. 2B not only generates a distinct pulse having a particular timing and amplitude, but also indicates that the existence of fissure 220 can cause a change in the amplitude of the back-surface return pulse 630, which is generally to be expected given that the fissure return pulse 220 utilizes energy that would have otherwise been used for the back-surface return pulse 630.

Figure 6C:
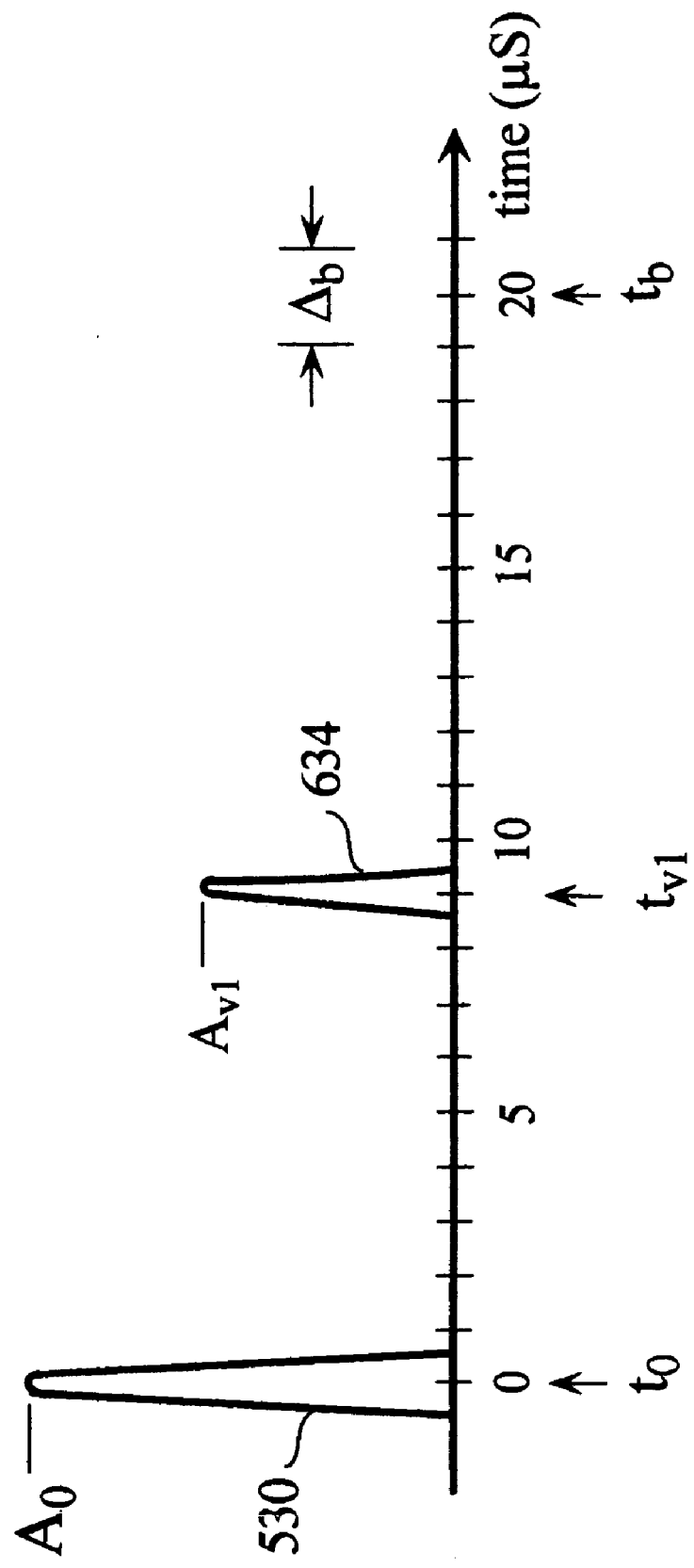

FIG. 6C is a timing diagram represent a third echo-profile that might be expected from the moderately damaged laminate structure of FIG. 2C taking into account the effects of void 230. As shown in FIG. 6C, the third echo-profile includes an outgoing pulse 530 as well as a void return pulse 634 (occurring at time $t_{v1}$ and having an amplitude $A_{v1}$) that results from the outgoing pulse bouncing off the front-surface of void 230. While the echo-profile of FIG. 6C depicts an intermediate pulse occurring between the outgoing pulse time ($t_0$) and the expected time of the back-surface return pulse ($t_b$) it should be noted that the echo-profile of FIG. 6C depicts no energy at the 20 microsecond mark. Such a complete absence of a back-surface return pulse is caused by the relevant physics of the situation, i.e., voids will generally not allow the passage of ultrasonic energy from one side to the other.

A review of FIGS. 6B and 6C reveal two significant points. The first point being that a particular area of damage can be categorized as a fissure verses a void based on whether an expected back-surface return pulse is substantially attenuated verse completely eliminated, and that the relative depth of the damaged area can be determined based on the relative timing of a return pulse. For example, the return time ($t_{f1}$) of the fissure return pulse 632 of FIG. 6B indicates that the fissure has occurred at a relatively shallow depth of 6 mm below the surface 120 of laminate structure 100, while the timing of the void return pulse ($t_{v1}$) indicates that the void is roughly in the center of the substrate 100 occurring approximately 13-14 mm below the front-surface 120. Accordingly, it should be appreciated that echo-profiles can not only provide an indication that damaged has occurred, but also can provide indication of the particular type of damage as well as the depth of the damage, which may be information useful to a technician or field engineer who must determine whether the laminate structure can be repaired on-site or must be returned to a particular facility having repair facilities.

Figure 6D:
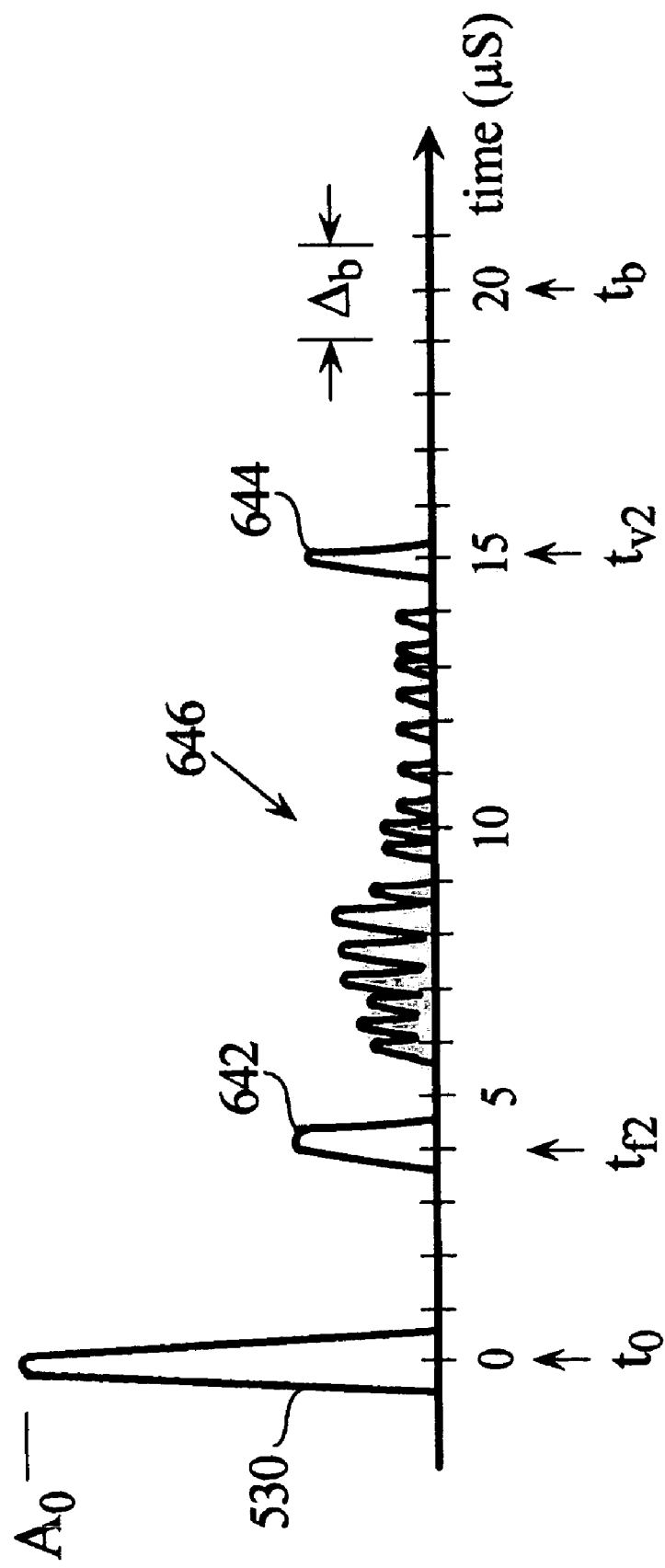

FIG. 6D is a timing diagram depicting an echo-profile as might be expected from a severely damaged laminate structure, such as the damaged depicted on FIG. 2D. As shown on FIG. 6D the echo-profile includes the outgoing pulse 530, a fissure return pulse 642, a void return pulse 644 and an amount of exemplary clutter 646.

Regardless of the severe amount of clutter and damage represented in FIGS. 2D and 6D, it should be appreciated that the echo-profile shown in FIG. 6D can reveal substantial information upon closer analysis. For example, the return pulse 642 shown at time $t_{f2}$ indicates that an appreciable fissure is present a few millimeters below the front-surface 120, as opposed to a void as a void would eliminate any substantial echo information after time $t_{f2}$. Conversely, using similar rationale pulse 644 can be determined as a void return pulse as there is little or no signal of any type detected after time $t_{v2}$. Additionally, as with the previous example, the timing of the fissure return pulse 642 indicates fissure damage occurring at a depth of 6 mm and further indicates that there is a void damage location occurring at a depth of about 22-23 mm below the front-surface of a laminate structure.

Figure 7:
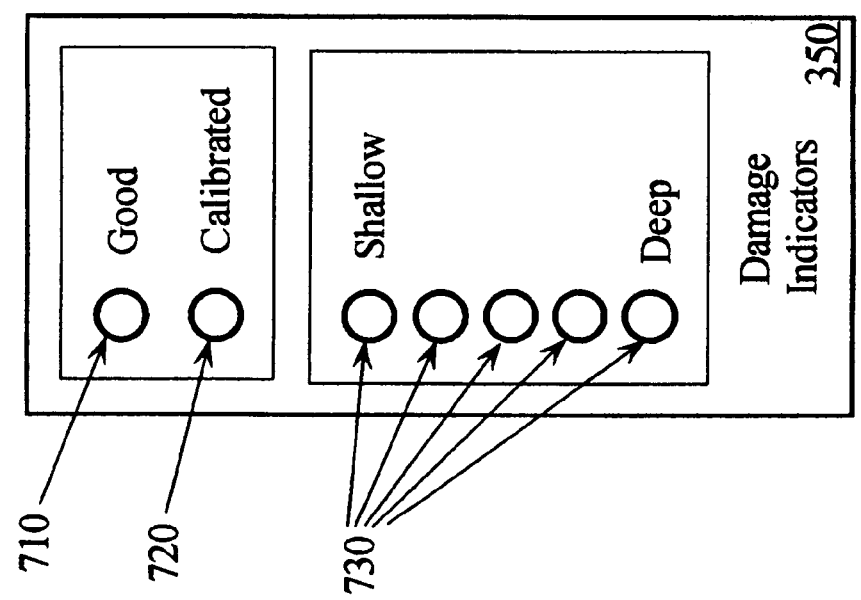
FIG. 7 depicts an exemplary display incorporated within the diagnostic tool of FIG. 3.

FIG. 7 is an exemplary diagnostic display 350 capable of being used in the diagnostic 300 of FIG. 3 and capable of displaying various amounts of relevant information. As shown in FIG. 7, the display 350 has a first indicator 710 that can be used to indicate whether a particular portion of a laminate structure is deemed to be undamaged, and also includes a second indicator 720 that can be used to provide an indication that the diagnostic device has recently been calibrated against a known, undamaged substrate.

In the exemplary embodiment, indicators 710 and 720 are but simple LED's. However, in other embodiments the exemplary indicators 710 and 720 can be multicolored LED's, e.g., green for good/undamaged and red for damaged. In, still further embodiments, the indicators can take the form of a portion of a liquid crystal display or any other display capable of displaying the various information relevant to the methods and systems of this disclosure.

In addition to the first two indicators 710 and 720, the diagnostic display 350 also includes a number of "damage depth" indicators 730, which can provide both an indication of the type of damage as well as the relative depth that such damage occurs in relation to the front and back-surfaces of a laminate. For example, in an undamaged laminate all of the damage indicators can remain deactivated. However, in instances of light damage such as that shown FIG. 2B, the top LED might be activated to indicate the detection of a shallow fissure. In contrast, the void 230 of FIG. 2C could cause the third/middle depth indicator to activate to inform an operator that there is damage in the middle of a laminate structure, and possibly activate in a different way, e.g., using a different color or blinking rate, to indicate a void has occurred as opposed to a fissure. In still other situations, such as that depicted by the heavily damaged substrate in FIG. 2D with its echo-profile shown in FIG. 6D, the various damage indicators can be appropriately activated to represent the shallow fissure return pulse 642 and the relatively deep void return pulse 644 by using the first and fourth damage depth indicators 730 activated in distinctly different ways.

Figure 8:
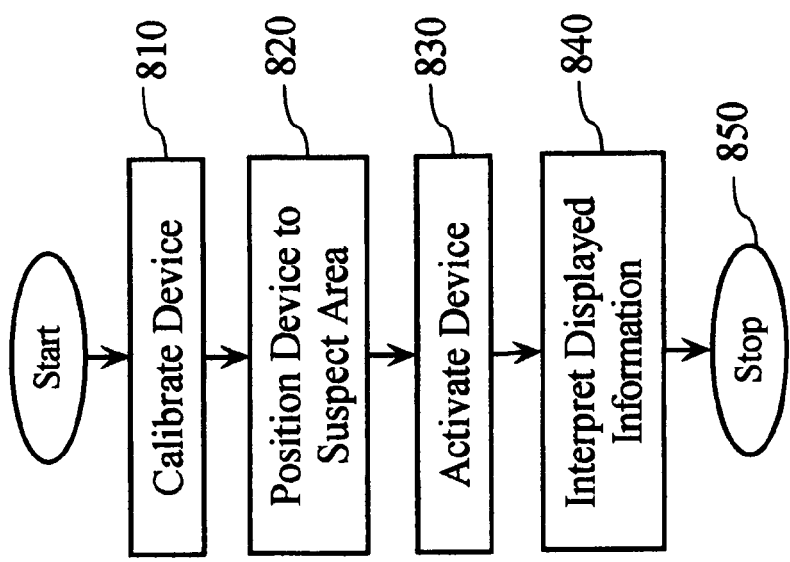
FIG. 8 is a flowchart outlining a first exemplary operation according to the present disclosure.

FIG. 8 is a flowchart outlining an exemplary operation according to the present disclosure for using a diagnostic device, such as the diagnostic tool 300 shown in FIG. 3. The process starts at step 810 where a diagnostic device is calibrated using an undamaged portion of a laminate structure. As discussed above, such calibration can be accomplished in a single round of outgoing and return pulse or alternatively can be accomplished using a series of outgoing and return pulses to assure statistically consistent and accurate calibration data. Control then continues to step 820.

In step 820, the operator then positions the diagnostic device to a suspect area of the laminate that may have a latent damaged portion beneath the surface. Next, in step 830, the operator can activate the diagnostic device to test the suspect area using the previously determined calibration parameters as testing criteria. As discussed above, such testing can take the form of a single round of outgoing and return pulses or alternatively can take the form of a plurality of outgoing and return pulses with appropriate statistical processing) to assure better accuracy. Control then continues to step 840.

In step 840, the operator can review, analyze and make determinations based on the displayed information. While the exemplary operation envisions that displayed data will generally conform to that with regard to FIGS. 3 and 7 it should be appreciated that in various embodiments it is entirely foreseeable to use other displays. Control then continues to step 850 where the process stops.

Figure 9:
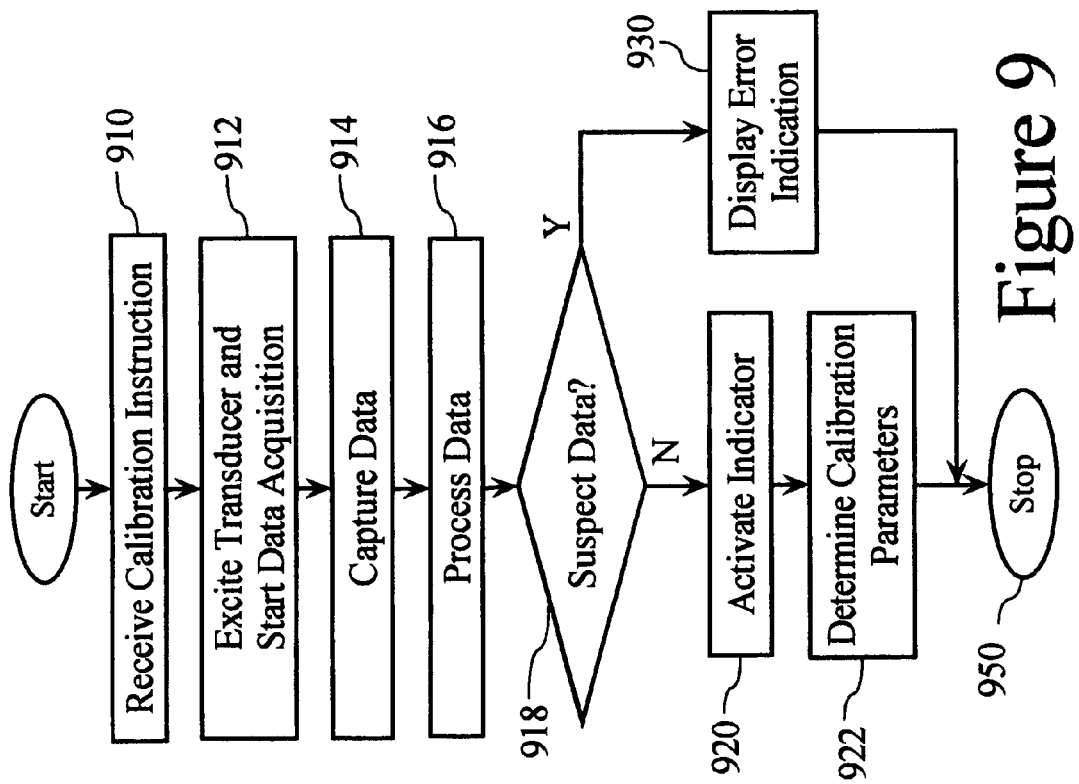
FIG. 9 is a flowchart outlining a second exemplary operation according to the present disclosure.

FIG. 9 is a flowchart outlining an exemplary operation for calibrating a diagnostic device according to the present disclosure. The process starts at step 910 where a diagnostic device, such as the diagnostic device 300 of FIG. 3, receives a calibration instruction. Next, in step 912, in response to the received instruction an ultrasonic transducer is excited to produce an outgoing ultrasonic pulse, and a data acquisition process is started such that any outgoing and return pulse energies can be detected and stored. Then, in step 914 the outgoing and return pulse energies are appropriately detected and captured. As discussed above, it may be desirable to use only a single round of outgoing and return pulse to perform a calibration cycle or may alternatively be desirable to employ a plurality of outgoing and return pulses to make the appropriate calibration determinations. Accordingly, steps 912 and 914 can be repeated as necessary to satisfy such criteria. Once the appropriate data has been captured, control then continues to step 916.

In step 916, the data captured in the previous steps can be appropriately processed to determine a number of calibration parameters including parameters relating to the timing and amplitude of a back-surface return pulse. Control then continues to step 918.

In step 918, the determination is made as to whether the data captured and processed in the previous steps is suspect. That is, whether the data is consistent with an undamaged substrate or whether the data captured is indicative of a substrate having internal damage. If the data is suspect, control continues to step 930: otherwise, control continues to step 920.

In step 920, which assumes that the data captured and processed during the calibration cycle conforms with an undamaged substrate, an indicator can be activated notifying an operator that a calibration cycle has been performed and that the resultant calibration data is consistent with an undamaged substrate. Next, in step 922, the relevant calibration parameters, e.g., parameters indicative of the the amplitudes and timing of the outgoing and return pulses, can be determined. Control then continues to step 950 where the process stops.

In step 930, which assumes that the data generated during a calibration cycle is suspect, i.e., that the data that was captured is consistent with a damaged substrate, an appropriate error indication is displayed to an operator, and control then continues to step 950 where the process stops.

Figure 10:
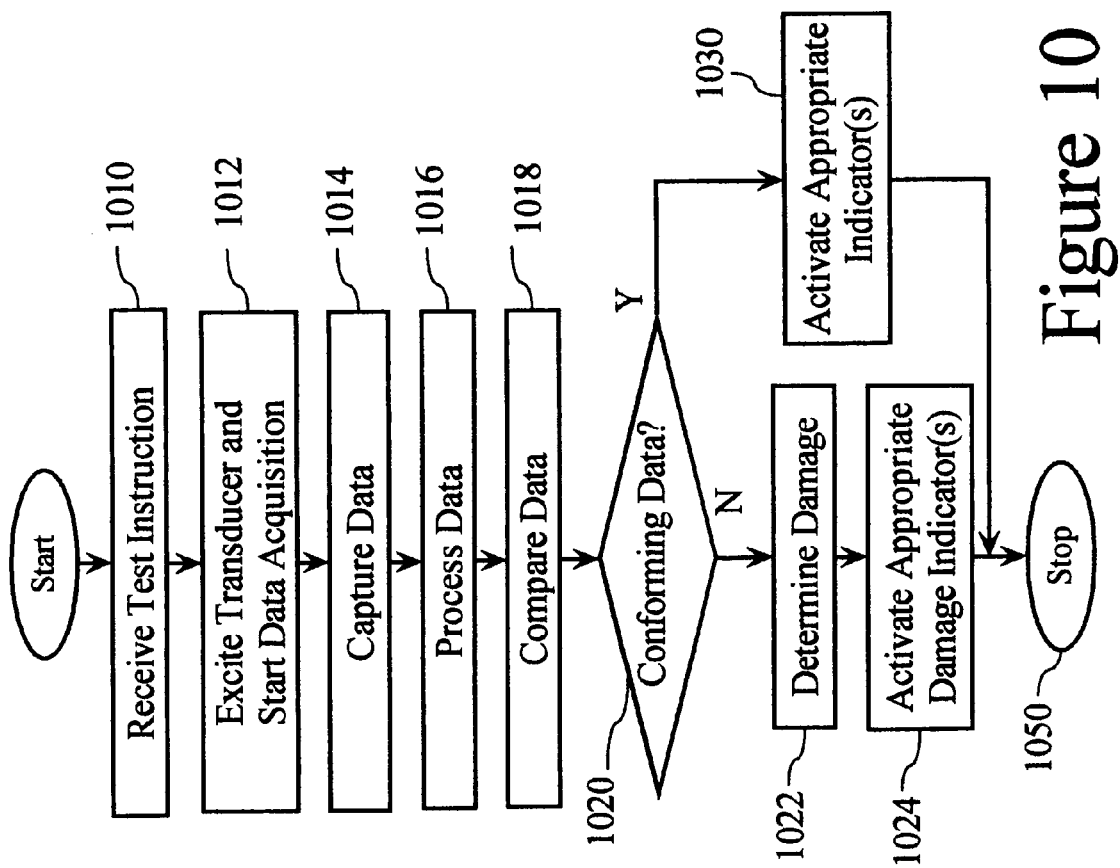
FIG. 10 is a flowchart outlining a third exemplary operation according to the present disclosure.

FIG. 10 is a flowchart outlining an exemplary operation according to the present disclosure, for an exemplary test cycle. The process starts in step 1010 where an instruction to start a test cycle is received. Next, in step 1012, an ultrasonic transducer is excited and a data acquisition process is started in response to the instruction. Then, in step 1014, the appropriate data covering one or more rounds of outgoing and return pulse is captured. As with the analogous calibration steps 912 and 914, it may be desirable to employ a single round or multiplicity of rounds of measuring outgoing and return pulses. Control then continues to step 1016.

In step 1016, the data captured in step 1014, is appropriately processed to look for any significant return pulses, their peak energies and relative timing with respect to a respective outgoing pulse. Next, in step 1018, the data captured and processed in the above steps is compared against a number of calibration parameters. Then, in step 1020, a determination is made as to whether the data captured and processed during the test cycle conforms with the calibration parameters. If the test data appropriately conforms, control jumps to step 1030: otherwise; control continues to step 1022.

In step 1030, which assumes that the test data substantially conforms with the calibration parameters and/or that no unexpected return pulses were received, an appropriate indicator is activated, and control continues to step 1050 where the process stops In contrast, in step 1022 which assumes that the test data did not conform to the calibration parameters, and/or that various ultrasonic artifacts indicating internal damage were detected, the type of damage, i.e., fissure or void, as well as the depth of damage is determined. Next, in step 1024, appropriate damage indicators are activated indicating whether damage has occurred, and optionally indicating the type and relative depth of such damage. Control then continues to step 1050 where the process stops.

While the above steps of the test cycle 1010 through 1050 are depicted as occurring a single time, it should be appreciated that in various embodiments the test cycle of FIG. 10 can take the form continuously repeated process thus enabling an operator to envision a profile of latent damage as the operator slides his diagnostic tool across the surface of a laminate structure.

In various embodiments where the above-described systems and/or methods are implemented using a programmable device, such as a computer-based system or programmable logic, it should be appreciated that the above-described systems and methods can be implemented using any of various known or later developed programming languages, such as "C", "C++", "FORTRAN", Pascal", "VHDL" and the like.

Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform the above-described systems and/or methods.

For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods to test laminate structures.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for evaluating damage to a laminate structure having a front-surface and a back-surface, the method comprising:
    calibrating a diagnostic device using an undamaged portion of the laminate structure to determine a plurality of calibration parameters in response to a transducer being pressed against the undamaged portion of the laminate structure and only a calibration button being pressed, wherein the calibration parameters include a return calibration pulse amplitude and a return calibration pulse timing;
    performing one or more test cycles to a suspect portion of the laminate structure using the one or more of the calibration parameters in response to the transducer being pressed against the suspect portion of the laminate structure and only an activation button being pressed, wherein the one or more test cycles includes transmitting a pulse into the laminate structure and sensing a plurality of test parameters, the test parameters including a return testing pulse amplitude and a return testing pulse timing;
    comparing the return calibration parameters to the test parameters; and
    activating a damage indicator in response to the comparison of the return calibration parameters to the test parameters exceeding a predetermined acceptable difference.

2. The method of claim 1, wherein the diagnostic device emits an ultrasonic pulse having a first frequency, and wherein the diagnostic device is configured to detect returned pulse energy of the first frequency.

3. The method of claim 2, wherein the first frequency is between from about 2.5 MHz to about 10 MHz.

4. The method of claim 3, wherein the first frequency is about 5 MHz.

5. The method of claim 2, wherein the emitted ultrasonic pulse has a generally bell-shaped amplitude profile.

6. The method of claim 1, wherein the step of calibrating includes touching the diagnostic device to the surface of the laminate structure at the undamaged portion.

7. The method of claim 6, wherein performing a test cycle includes touching the diagnostic device to the surface of the laminate structure at the suspect portion.

8. A method for ultrasonically testing a laminate structure having a front-surface and a back-surface, the method comprising:
    performing a test cycle on a suspect portion of the laminate structure based on an ultrasonic echo-profile in response to a transducer being pressed against the suspect portion of the laminate structure and only an activation button being pressed;
    comparing test cycle parameters to calibration parameters, the test cycle parameter including a return test cycle pulse amplitude and a return test cycle pulse timing, the calibration parameters including a return calibration pulse amplitude and a return calibration pulse timing;
    determining whether the suspect portion of the laminate structure conforms to the calibration parameters, the calibration parameters providing information about an undamaged portion of the particular laminate structure under test; and
    activating a damage indicator in response to the suspect portion not conforming to the calibration parameters.

9. The method of claim 8, further comprising determining a type of damage based on the echo-profile.

10. The method of claim 8, further comprising determining damage depth based on the echo-profile.

11. A method for calibrating a diagnostic device capable of detecting latent damage in a laminate structure, the method comprising:
    emitting an ultrasonic pulse into the laminate structure in response to the diagnostic device being pressed against the undamaged portion of the laminate structure and only a calibration button being pressed;
    detecting an echo-profile of the laminate structure in response to the emitted ultrasonic pulse; and
    determining a plurality of calibration parameters in response to the detected echo-profiles, the calibration parameters providing information about an undamaged portion of the laminate structure under test, wherein the calibration parameters include a return calibration pulse amplitude and a return calibration pulse timing and wherein the calibration parameters are compared to a plurality of test parameters to test the laminate structure, the test parameters including a return testing pulse amplitude and a return testing pulse timing.

12. A laminate diagnostic apparatus, comprising:
    a laminate measuring means for sonically evaluating a laminate structure in response to the laminate diagnostic apparatus being pressed against the laminate structure and only an activation button being pressed, the laminate measuring means comprising:
        a pulse generating means to generate a pulse;
        a pulse sensing means to sense a return pulse amplitude and a return pulse timing; and
        a comparing means to compare the return pulse amplitude and the return pulse timing to a calibration pulse amplitude and calibration pulse timing; and
    a display means coupled to the measuring means for providing a damaged/not damaged indication of the laminate structure based on a signal from the measuring means.

13. The laminate diagnostic apparatus of claim 12, wherein the measuring means employs a calibration cycle for measuring an undamaged portion of the laminate structure.

14. The laminate diagnostic apparatus of claim 13, wherein the measuring means further employs a test cycle for evaluating a suspect portion of the laminate structure.

15. The laminate diagnostic apparatus of claim 14, wherein the measuring means uses information about the laminate structure developed during the calibration cycle to evaluate the laminate structure during the test cycle.

16. The laminate diagnostic apparatus of claim 12, wherein the display means provides a damaged/undamaged indication.

17. The laminate diagnostic apparatus of claim 16, wherein the display means further provides a depth indication of a damaged portion within the laminate.

18. The laminate diagnostic apparatus of claim 17, wherein the display means further provides a damage-type indication of the damaged portion.

19. A diagnostic apparatus for evaluating an amount of damage to a laminate structure, comprising:
   a test manager coupled to a data-acquisition device and a sonic transducer;
   wherein the diagnostic apparatus compares a calibration cycle and a test cycle, the calibration cycle including a pulse amplitude calibration and a pulse timing calibration, the test cycle including a pulse amplitude test and a pulse timing test, wherein the calibration cycle produces a plurality of calibration parameters in response to the diagnostic apparatus being pressed against the laminate structure and only a calibration button being pressed, and wherein the test cycle uses the one or more of the calibration parameters to evaluate whether a portion of the laminate structure is damaged in response to the diagnostic apparatus being pressed against the laminate structure and only an activation button being pressed.

20. The diagnostic apparatus of claim 19, wherein the calibration parameters provide information about an undamaged portion of the particular laminate structure under test.

* * * * *